(12) United States Patent
Tom

(10) Patent No.: US 8,313,443 B2
(45) Date of Patent: Nov. 20, 2012

(54) TENSIOMETER UTILIZING ELASTIC CONDUCTORS

(76) Inventor: Michael D. Tom, Greenwich, CT (US)

( * ) Notice: Subject to any disclaimer, the term of this patent is extended or adjusted under 35 U.S.C. 154(b) by 232 days.

(21) Appl. No.: 12/720,428

(22) Filed: Mar. 9, 2010

(65) Prior Publication Data

US 2010/0228157 A1 Sep. 9, 2010

Related U.S. Application Data

(60) Provisional application No. 61/209,636, filed on Mar. 9, 2009.

(51) Int. Cl.
- A61B 5/03 (2006.01)
- A61B 5/11 (2006.01)
- H01L 29/84 (2006.01)
- B32B 27/12 (2006.01)

(52) U.S. Cl. ........ 600/561; 252/511; 257/415; 257/417; 428/340; 600/587

(58) Field of Classification Search .......... 252/511; 73/763; 600/587, 561; 428/340; 257/415, 257/417

See application file for complete search history.

(56) References Cited

U.S. PATENT DOCUMENTS

| | | | |
|---|---|---|---|
| 6,809,462 B2 | 10/2004 | Pelrine et al. | |
| 6,848,320 B2 | 2/2005 | Miyajima et al. | |
| 7,146,203 B2 * | 12/2006 | Botvinick et al. | 600/345 |
| 7,354,988 B2 | 4/2008 | Charati et al. | |
| 7,402,264 B2 | 7/2008 | Ounaies et al. | |
| 7,460,224 B2 * | 12/2008 | Wang et al. | 356/301 |
| 7,576,854 B2 * | 8/2009 | Wang et al. | 356/301 |
| 7,733,479 B2 * | 6/2010 | Shew et al. | 356/244 |
| 7,955,559 B2 * | 6/2011 | Joshi et al. | 422/68.1 |
| 8,039,834 B2 * | 10/2011 | Wang et al. | 257/43 |
| 8,102,096 B2 * | 1/2012 | Makansi | 310/306 |
| 2003/0096104 A1 | 5/2003 | Tobita et al. | |
| 2004/0258604 A1 * | 12/2004 | Ryzhkov | 423/445 R |
| 2006/0241365 A1 * | 10/2006 | Botvinick et al. | 600/345 |
| 2006/0253942 A1 | 11/2006 | Barrera et al. | |
| 2007/0138010 A1 | 6/2007 | Ajayan | |
| 2007/0208243 A1 * | 9/2007 | Gabriel et al. | 600/347 |
| 2008/0058467 A1 * | 3/2008 | Takagi et al. | 524/588 |
| 2008/0067618 A1 * | 3/2008 | Wang et al. | 257/415 |
| 2008/0135813 A1 * | 6/2008 | Kaneko et al. | 252/502 |
| 2008/0292887 A1 | 11/2008 | Kim et al. | |
| 2009/0084678 A1 * | 4/2009 | Joshi et al. | 204/403.14 |
| 2009/0099433 A1 * | 4/2009 | Staib et al. | 600/345 |
| 2009/0101498 A1 * | 4/2009 | Papadimitrakopoulos et al. | 204/403.11 |
| 2009/0221782 A1 | 9/2009 | Dupire et al. | |
| 2009/0309172 A1 | 12/2009 | Liu et al. | |

* cited by examiner

Primary Examiner — Sean Dougherty
(74) Attorney, Agent, or Firm — St. Onge Steward Johnston & Reens LLC

(57) ABSTRACT

A tensiometer is an elastic conductor which comprises a mixture of an elastomer and carbon nanotubes. The tensiometer has a reproducible conductivity in order to measure and change in shape and tension of an object to which it is applied. The tensiometer is non-toxic and may be implanted into a human body.

28 Claims, 10 Drawing Sheets

TENSIOMETER UTILIZING ELASTIC CONDUCTORS

CROSS-REFERENCE TO RELATED APPLICATIONS

This patent application claims the benefit, under 35 U.S.C. §119(e), of U.S. Provisional Patent Application Ser. No. 61/209,636, filed on Mar. 9, 2009, which is hereby incorporated by reference herein.

FIELD OF THE INVENTION

The present teachings relate to tensiometers and, more particularly, non-toxic tensiometers comprising an elastomer-nanotube mixture for implantation in mammals.

BACKGROUND OF THE INVENTION

A tensiometer is an instrument for measuring stress in objects. It may be constructed from conductive material having conductivity that changes in a predictable or reproducible way as its shape changes (e.g., as it is stretched, etc.). In this way, the tensiometer may be applied to the surface of an object and measure stress thereon by the changing conductivity of the tensiometer.

A tensiometer may be constructed from an elastic conductor so that it can be applied to objects having any number of different shapes. Elastic conductors are an extremely new field of science. They have been constructed with complex chemical procedures that involve various toxic components.

Therefore, it would be beneficial to have a superior tensiometer and method of manufacture.

SUMMARY OF THE INVENTION

The needs set forth herein as well as further and other needs and advantages are addressed by the present embodiments, which illustrate solutions and advantages described below.

The tensiometer of the present embodiment includes, but is not limited to: a mixture of an elastomer and carbon nanotubes, the mixture having substantially between 9 and 20% nanotubes by weight, although not limited thereto, and a circuit adapted for measuring conductivity across the tensiometer. The conductivity of the tensiometer increases as the tensiometer is stretched along an axis, the tensiometer has a reproducible conductivity suitable for measuring changes to the tensiometer's stretch which the circuit measures by corresponding changes in the tensiometer's conductivity, and the tensiometer is non-toxic and suitable for implanting in a mammal for measuring change in tension.

Other embodiments of the system and method are described in detail below and are also part of the present teachings.

For a better understanding of the present embodiments, together with other and further aspects thereof, reference is made to the accompanying drawings and detailed description, and its scope will be pointed out in the appended claims.

DETAILED DESCRIPTION OF THE INVENTION

Figure 1:
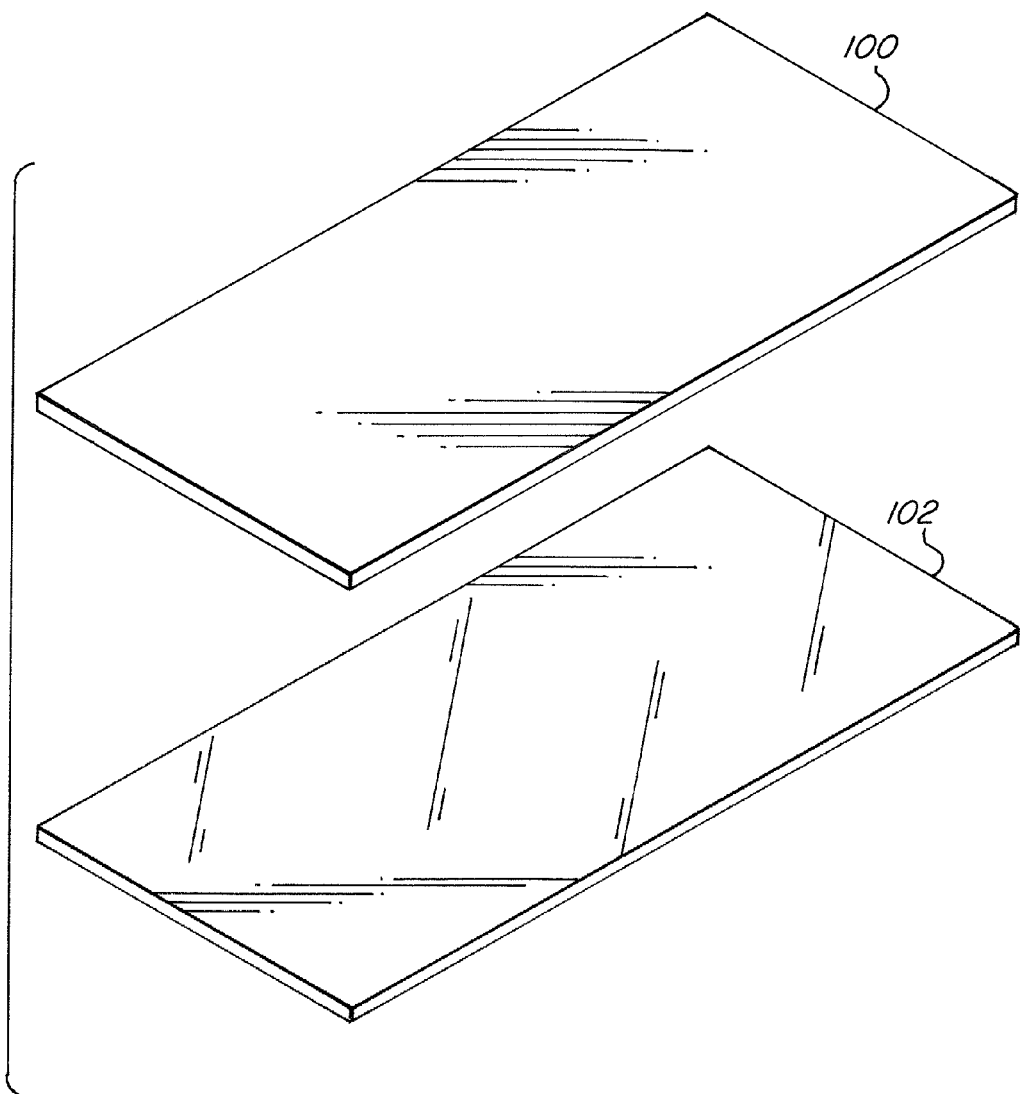
FIG. 1 is a top view depicting one embodiment of the tensiometer according to the present teachings shown with a pure elastomer strip.

The present teachings are described more fully hereinafter with reference to the accompanying drawings, in which the present embodiments are shown. The following description is presented for illustrative purposes only and the present teachings should not be limited to these embodiments.

In one embodiment according to the present teachings, the tensiometer comprises an elastic conductor manufactured by mixing an elastomer with carbon nanotubes. An elastomer is an elastic polymer which may be a synthetic rubber. Typically, it has long polymer chains that cross-link during curing. Elasticity is due to the ability of the long chains to reconfigure themselves to distribute an applied stress. The cross links ensure that the elastomer will return to its original configuration when the stress is removed. Very few materials can adhere and successfully mix with elastomers. Consequently, they are often used in electrical applications as insulators and sealants.

Carbon nanotubes are allotropes of carbon with cylindrical nanostructures. They have a very large effective surface area and are ideal for dispersion into an elastomer. Nanotubes naturally align themselves into "ropes" held together by Van der Waals forces. They exhibit extraordinary strength, unique electrical properties, and are efficient thermal conductors. When dispersed in an elastomer they have a high probability of connection with one another, which permits electrical conductivity through the elastomer.

The use of ionic liquid, discussed further below, has been shown to decrease the conductivity of the material. Since ionic liquid is not necessary and carbon nanotubes are chemically inert, the tensiometer described herein may be nontoxic. This increases its range of use. For example, long cylinders of conductive elastomer can be woven into human muscle or tissue since the material's inertness permits biocompatibility. It can also be molded into any shape due to its viscosity prior to curing.

A tensiometer manufactured from an elastomer-nanotube material has both high elasticity and conductivity. The tensiometer has a reliable and measurable change in conductivity (or, inversely, its resistance). By measuring this change in conductivity, the tensiometer can be used to accurately measure deformation caused by, for example, pressure, tension twisting, stretching, and compression, although not limited thereto. The formulas discussed below may be different for particular torsion forces and although lateral volume changes are discussed in particular, the present teachings are not limited thereto. When dispersing nanotubes into an elastomer, the elastomer chemical properties are retained even with increasing nanotube concentration.

The elastomer-nanotube material exhibits increasing conductivity with an increasing applied force. This is due to the increased contacts of carbon nanotubes within the dispersion as it stretches, as well as the effects of lateral separation of nanotube contacts and the increased length and decreased cross-sectional area the current travels.

At the molecular level, there is a threshold of nanotube concentration that must be achieved for conductivity since the nanotubes must make connections with each other throughout the elastomer. However, a tensiometer should not be excessively conductive because then the power dissipation would cause it to heat up. This would be undesirable in many circumstances, such as when the tensiometer is intended to be implanted in a human body. The properties of the elastomer-nanotube material are ideal for biocompatibility.

In one embodiment of the procedure for making the tensiometer, an elastomer is first mixed with carbon nanotubes. The elastomer polydimethylsiloxane may be used, but any other silicone based or other type of elastomer could be used. The elastomer may be Sylgard 184 Polydimethylsiloxane purchased from Dow Corning™, although not limited thereto.

The nanotubes may be multi-walled carbon nanotubes purchased from Sigma-Aldrich™, although not limited thereto. These nanotubes have a diameter of 110-170 nm with a length of 5-9 μm. Their purity is over 90% carbon with a density of 1.7 g/ml as a solid. There are many ways to produce carbon nanotubes, including laser ablation and arc discharge, although these are produced using catalytic vapor deposition (CVD). It is appreciated that any other nanotube could be used, whether single-walled or multi-walled, in any number of different lengths and dimensions, and the present teachings are not limited to this particular embodiment. Varying purities and concentrations of nanotubes may be used to achieve the desired qualities of elasticity and conductivity, preferable ranging from 2% to 20% of the mixture, although not limited thereto, which in one embodiment is measured by weight. Greater than 20% nanotube concentration has been found to have a viscosity that made the material hard to work with while 15% nanotube concentration was found to be most preferable.

The mixture of elastomer and nanotubes may be mixed and sonicated to enhance dispersion. However, any other method of mixing the ingredients may be used. Next, a catalyst may be added to the elastomer to accelerate polymerization. Catalyst 87-RC purchased from Dow Corning™ may be used, although any other type of catalyst may be used, or no catalyst at all.

Depending on the viscosity of the resultant material, which in some cases may be paste-like, it may be drop cast on glass or compressed between glass plates with metal spacers to ensure uniform thickness. For cylindrical casting, the liquid may be forced through a tube using vacuum pressure. It is appreciated that any number of different methods can be used to manufacture a tensiometer from the elastomer-nanotube material in any number of different shapes and the present teachings are not limited to this particular method.

The mixture may then be put into a vacuum pressure chamber to remove air pockets, although any other suitable method could be used for this purpose. Doing this provides a more uniform material. Due to the viscosity of the material, sonication may not fully achieve uniformity. Viscosity is at least partially dependent on the concentration of tubes, which is in turn dependant on the properties of the nanotubes. Therefore, if better quality tubes are used, sonication alone may be sufficient to remove any air cavities.

Finally, the mixture may be cured at 80 degrees C. for an hour to facilitate polymerization, although any other curing method is also possible. Referring now to FIG. 1, shown is a top view depicting one embodiment of the tensiometer 100 according to the present teachings shown with a pure elastomer strip 102. The cured elastomer-nanotube material manufactured according to the process above may be cut into any number of shapes in any number of desired dimensions. As shown, the tensiometer 100 is a rectangular strip suitable for measuring stretching along its length. It retains the preferable properties of a pure elastomer 102, such as its elasticity, yet is conductive due to the nanotube dispersion.

A large area of contact may be desired to obtain maximum conductivity across the tensiometer. A testing device can be used to measure current, electric potential, and applied force on the tensiometer. In one embodiment, conducting plates (e.g., aluminum, etc.) may be clamped to the ends of the tensiometer to maximize the surface area for the current to flow. In an alternative embodiment, wires may be embedded in the tensiometer to conduct electric current therethrough.

Figure 2:
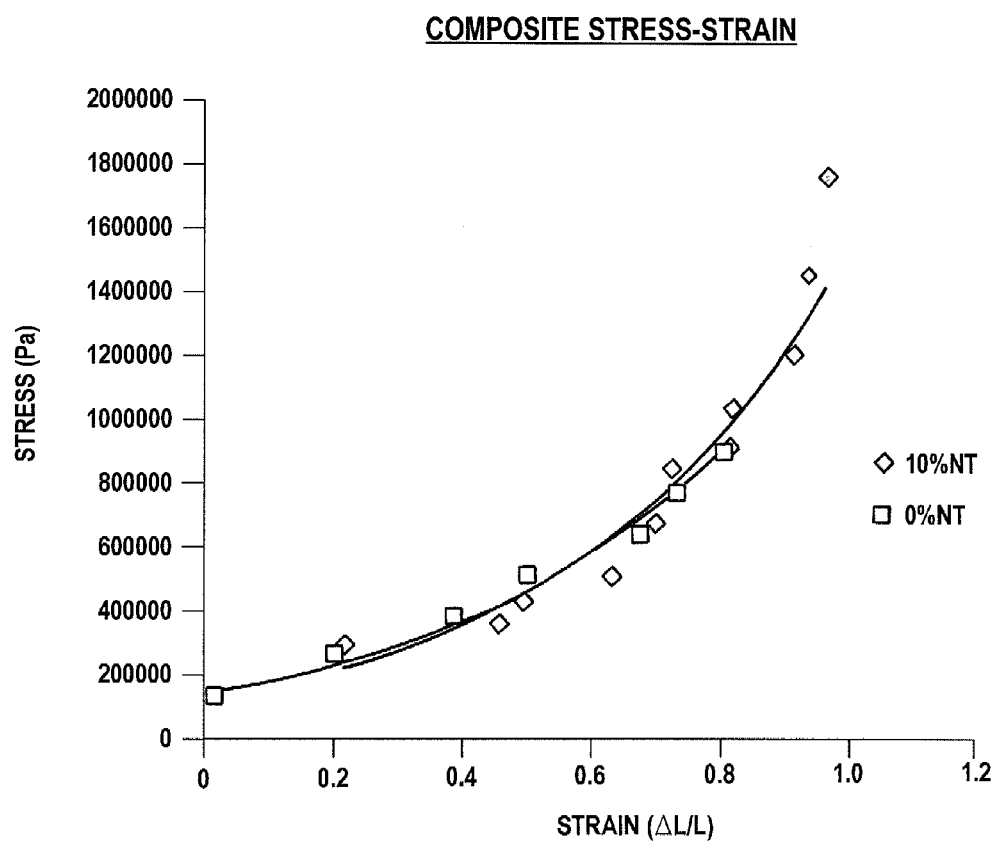
FIG. 2 is a graph depicting a comparison of the elastic properties of 0% nanotube material (pure elastomer) versus 10% nanotube material.

Referring now to FIG. 2, shown is a graph depicting a comparison of the elastic properties of a 0% nanotube material (pure elastomer) versus a 10% nanotube material. The elastic modulus (A) is the derivative of stress ($F/A_0$) with respect to strain ($\Delta L/L_0$), which is used in the calculations discussed below. The greater the elastic modulus (slope of the stress-strain curve), the less elastic the material is. Infrared spectra of a pure elastomer may be compared with one having 10% nanotube dispersion. The elastic properties of the elastomer are not significantly altered with nanotube concentration.

The output current across the tensiometer may be converted into forces readable by computers or sensors. An equation based on the equations for Young's modulus, Poisson's ratio, resistivity, and the derived stress-strain curve may be used. For elastomers and rubbers, the value for Young's modulus changes with increasing force. At very small strains there is a linear relationship, yet it turns into an exponential function until its yield strength is surpassed. The Young's modulus (E) for this particular elastomer varies exponentially. Poisson's ratio (V) may also be incorporated, which is the ratio of longitudinal to axial strain. In one embodiment, this value was measured at 0.37.

Such an equation holds true for conductors where the current moves along the molecules being stretched. However, the elastic conductor tensiometer described herein is a dispersion of carbon nanotubes within an insulator, and percolation theory is therefore preferably incorporated. Conductivity increases because of increased nanotube to nanotube contact with a decreasing total volume when the tensiometer is stretched. With greater pressure within a particular cross section, the nanotubes are bundled closer together which increases conductance. Percolation theory (determining the connectivity of randomly oriented objects) models connections between nanotubes and therefore conductivity. The conductance is expressed based on the conductivity of a single nanotube, the volume fraction, and critical percolation volume. Differential equations may be used to model the changes in conductance with stretching. Poisson's ratio may be generalized to find volume compression in the isotropic material. Quantum conductance also may occur, causing a small offset in the conductance that increases with stretching and decreased inter-nanotube distance.

$$v = -\frac{\text{strain}_{tranc}}{\text{strain}_{exist}} \qquad F = \frac{EA_0 \Delta L}{L_0}$$

$$R = \frac{l\rho}{A} \qquad \frac{F}{A_0} = Ce^{\frac{R\Delta L}{L_0}}$$

$$F = A_0 c e^{\frac{k}{v}\left(1 - \sqrt{\frac{R_0(1+k)}{k(R)}}\right)}$$

These equations may be used to provide theoretical force versus resistance for a single substance elastic material with inherent conductivity. F represents force, $A_0$ is the initial cross-sectional area, c and k are constants derived from the stress-strain curve, v is Poisson's ratio, $R_0$ is initial resistance, and R is final resistance.

The excluded area of a single nanotube has a direct relation to the percolation threshold and can be used to explain changes in conductivity due to magnetic alignment of the nanotubes. Excluded area depends on nanotube length, diameter, and disorder degree. A greater excluded area indicates a greater percolation threshold.

Self-organization of tubes into bundles affects the critical volume for percolation. Magnetic alignment decreases the conductivity and increases the percolation threshold because of reduced bundling and decreased randomness. Since the nanotubes are of different lengths, this must also be taken into account in determining the excluded area and hence the percolation threshold.

This equation may be used to find conductivity based on a changing volume:

$$\sigma = \sigma_{met}\left(\frac{V_{NT}}{\frac{dV}{dL}L(1-2v)} - \Phi_C\right)^n$$

V represents volume and L represents length. Exponent n is derived from the change on conductivity with nanotube fraction. This is in contradiction with the experimental results, signifying that the volume change may not be the only thing that affects nanotube to nanotube contacts. The self-assembly in nanotube bundles modeled separately can come into contact with each other.

Average excluded area calculations show an increase in the percolation threshold based on the topology of dispersed and oriented 3-D nanotubes. The dependant factor on alignment is y, the averaged angle between nanotubes throughout. Since more tubes are aligning in the field, the angle between them decreases and therefore the percolation threshold increases.

$$\Phi_C = \frac{V_{NT}}{\frac{4\pi}{3}W^3 + 2\pi W^3 + 2WL^2\langle \sin\gamma\rangle}$$

This may be used to show the ratio of nanotube volume to the excluded volume used to calculate a percolation threshold. The excluded area is based on the geometry of a tube and the relation between the average angle of the system.

Figure 3:
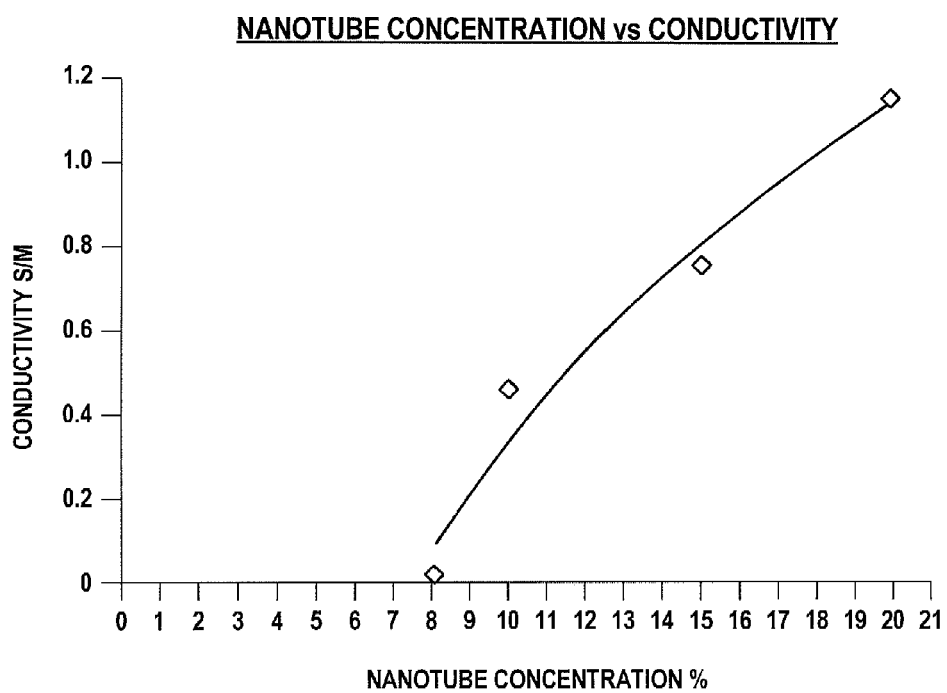
FIG. 3 is a graph depicting nanotube concentration versus conductivity in the tensiometer.

Referring now to FIG. 3, shown is a graph depicting nanotube concentration versus conductivity in the tensiometer. Nanotube concentration may be measured by weight, although not limited thereto. Conductivity may be shown to increase with nanotube concentration logarithmically in the effective dispersion range of 9-20% relative to the base elastomer. Below the threshold of 9% nanotubes, the material has been shown to have little or no conductivity because of insufficient junctures between nanotubes. With concentrations above 20%, it was difficult to manage the material and properly disperse the nanotubes within the elastomer. Shown is a sharp ramp up in conductivity at around 9% and then a logarithmic increase. In one embodiment, the percolation threshold in random dispersion was determined to be at 9% with a volume fraction (1) of 0.0445.

In one embodiment, the yield strength (when an elastic material permanently deforms) of a 15% nanotube dispersion was found to be 2.2 MPa, increasing linearly with increasing nanotube concentration. The tensiometer is very elastic with an elastic modulus ranging from 680 to 3,790 kPa (kilopascal) and a current of 11 mA (milliamp) through a 20% nanotube conductor was observed. Poisson's ratio is the measure of longitudinal strain (change in length divided by initial length) divided by lateral strain. This is an isotropic property. The Poisson's ratio was measured at 0.37 in one embodiment.

Figure 4:
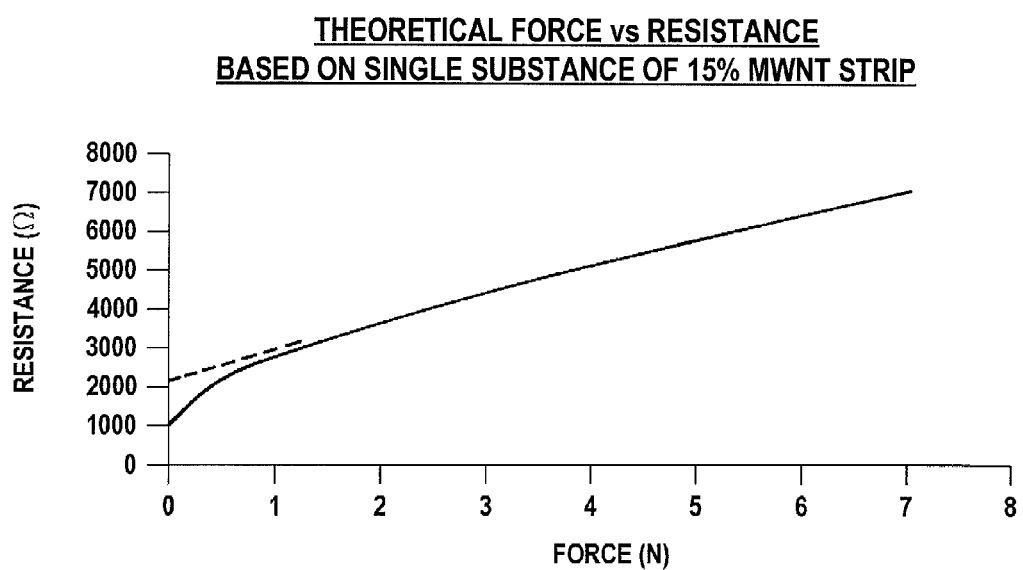
FIG. 4 is a graph depicting the theoretical resistance versus applied lateral force on a 15% nanotube tensiometer.

Referring now to FIG. 4, shown is a graph depicting the theoretical resistance versus applied lateral force on a 15% multi-walled nanotube (MWNT) tensiometer. The dotted line represents the values for small stresses when the Young's modulus increases linearly. A linear response is expected, and this is a calculated projection since resistance is expected to increase when force was applied. However, the actual results, discussed further below, show that the resistance decreased when force was applied by stretching the tensiometer lengthwise. The response is related to increased contact between the nanotubes when the device is stretched and therefore the nanotubes get squeezed closer together.

Figure 5:
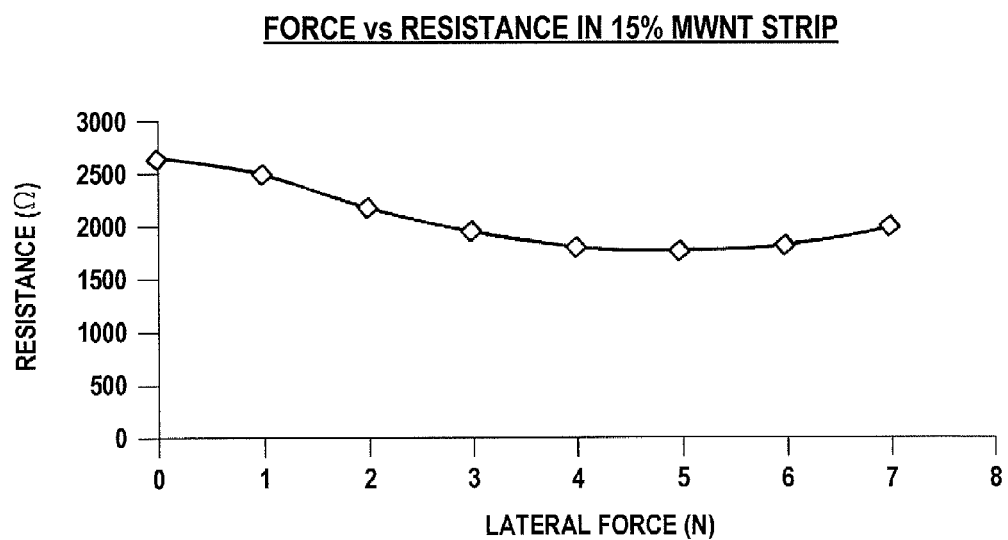
FIG. 5 is a graph depicting actual resistance versus applied lateral force on a 15% nanotube tensiometer.

Referring now to FIG. 5, shown is a graph depicting actual resistance versus applied lateral force on a 15% multi-walled nanotube (MWNT) tensiometer. Changes in conductivity/resistance of the elastomer-nanotube material are easily measurable with stress. In this case, a stretching force was applied to a strip tensiometer manufactured from the elastomer-nanotube material described herein. Force was applied to stretch it lengthwise while current and voltage were measured. Conductivity is shown to increase due to increased nanotube to nanotube contacts and quantum tunneling effects. With greater pressure within a particular cross section, the nanotubes are bundled closer together which increases conductivity. The minimum of the graph shown in FIG. 5 represents the point at which the increase of conductance from nanotube connections is overcome by the decrease of conductance from increased length of the polymer and lateral separation of tubes.

Variables intended to change conductivity may be considered, including magnetic alignment and the addition of ionic liquid. These demonstrate the importance of nanotube bundling for conductance. Magnetic alignment of nanotubes, for example, has been shown to change conductivity of the tensiometer, depending on its angle from the direction of current, of up to a factor of 2, although not limited thereto.

In order to prevent the nanotubes from bundling (their natural tendency due to Van der Waals forces) ionic liquid 1-Butyl-3-methylimidazolium bis(trifluoromethylsulfonyl) imide may be mixed with the nanotubes before dispersion in the elastomer. However, the addition of the ionic liquid significantly reduces conductivity.

A solution coating with cobalt nitrate may be used to amplify the dipole magnetization of the nanotubes. In this way, a clear water-insoluble liquid such as toluene may partially dissolve the elastomer around the nanotubes. This is preferably performed on the nanotubes before their dispersion in the elastomer.

Magnetic alignment can be used to vary conductivity of the nanotubes according to the angle of the introduced magnetic field. After catalyzing, a magnetic field may be applied to the elastomer-nanotube mixture. The torque exerted on the nanotubes by the magnetic field is strong enough to rotate them through the viscous elastomer. This alters the random distribution of nanotubes within the polymer because the magnetic force overcomes the Van der Waals forces between nanotubes.

Magnetization may be done with bar magnets, but could also be done with any form or strength of magnets. The mixture may be placed in a magnetic field at different angles to its long axis before curing to align the nanotubes. In a percolation model the disorder degree of nanotubes is decreased. However, there is a correlation between the orientation of the nanotubes with respect to the direction of current. This finding indicates that conductivity within a carbon nanotube-based conductor can be altered after curing without the need of additional doping.

The finding that magnetic alignment alters conductivity can lead to very important applications in the field of nanotube-based conductors. This signifies the ability to successfully change conductivity without the addition of a doping agent. For example, silicon semiconductors require the use of chemical impurities in order to change from insulator to conductor. Magnetic alignment shows the potential to create elastic semiconductors using magnetism in place of a doping agent.

Figure 6:
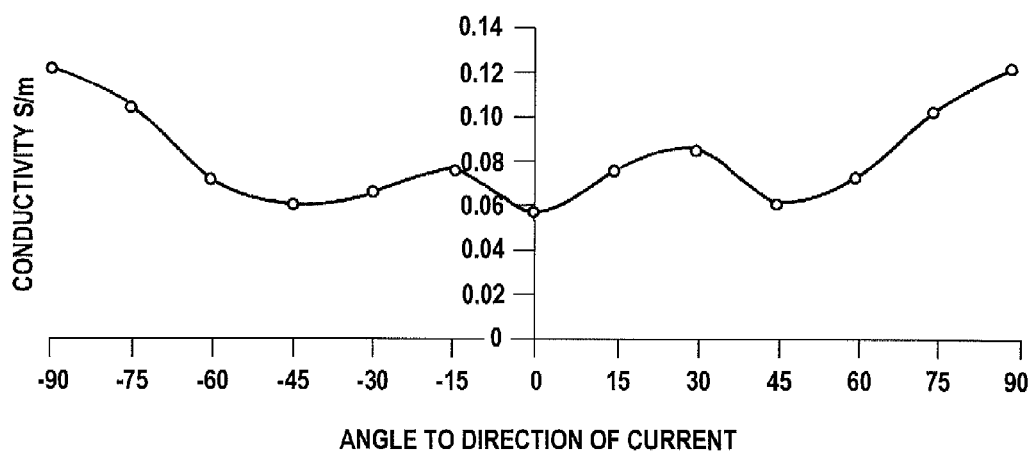
FIG. 6 is a graph depicting the change of conductivity versus the angle of magnetic alignment of the nanotubes in the tensiometer after forming the material but before curing and polymerization.

Referring now to FIG. 6, shown is a graph depicting the change of conductivity versus the angle of magnetic alignment of the nanotubes after forming the material but before curing and polymerization. This graph shows that magnetic alignment of nanotubes can be used as a way of changing conductivity. Previous research has indicated that magnetic fields with strengths of up to 1 Tesla are needed to fully align nanotubes coated with metallic ions. However, this demonstrates a change in conductance without the need of metallic ion coating at much lower magnetic field strengths.

A flexible conductor is advantageous compared to a rigid one in many situations, such as when used to cover an arbitrarily curved surface or moving part. There may be further applications for the tensiometer described herein, such as an elastic conductive sheet which can provide complete coverage in a smart skin for prosthetic limbs and robots, although not limited thereto. The tensiometer is ideal for incorporation into medical devices that can assess tissue tension, whether on the bladder, or anywhere else on or in the body. This was not possible previously without elastic conductors because of the complex movements of the body and internal organs.

One application for the tensiometer described herein is to measure bladder wall tension in patients with bladder conditions. These include neurogenic bladder, a dysfunction where patients cannot sense bladder fullness because of disease or injury affecting the bladder's natural stretch receptors. A non-toxic tensiometer could provide an indication of bladder fullness, and interface with an implantable neural stimulator for improved bladder control.

Current management of neurogenic bladder includes self-catheterization, artificial sphincters, and stoma creation for external drainage of urine. These treatments are uncomfortable and increase the risk of infection. Other methods require various imaging techniques such as ultrasound or CT scans. These measurements are static and are not feasible for daily assessment. Methods to reestablish the ability to sense bladder fullness with a tensiometer could improve the quality of life for these patients.

Pressure sensors cannot be indwelling or accurately measure bladder urine volume. In the human bladder there is no linear relationship between pressure within the bladder and the volume of the bladder. Instead, the pressure remains constant but the volume of the bladder contents increases several times. The tensiometer is ideal for these measurements, as it would not be possible to measure specific bladder fullness using internal pressure sensors. The tensiometer can measure bladder fullness more accurately, less expensively, and with greater continuity than presently possible.

Figure 7:
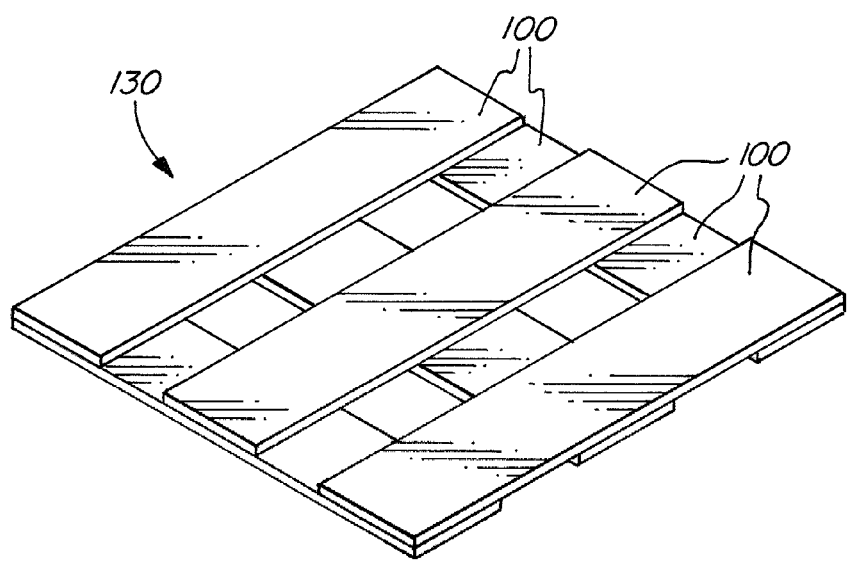
FIG. 7 is a top view depicting one embodiment of a patch design of the tensiometer according to the present teachings.

Referring now to FIG. 7, shown is a top view depicting one embodiment of a patch design tensiometer 130 according to the present teachings. In this embodiment, the patch design tensiometer 130 may have several strips of individual tensiometers 100 arranged perpendicularly, or they could be at other angles to each other, and various numbers of strips of various lengths and widths could be used. The tensiometer could be constructed in this way in order to measure the change of shape (e.g., stretch, etc.) of a curved surface, such as a human bladder. Each individual tensiometer 100 can be individually monitored so that multiple directions can measured simultaneously. In one embodiment, although not limited thereto, each individual tensiometer 100 may be encased in a thin layer of elastomer to ensure minimal toxicity, and prevent current contamination and thermal power dissipation.

Figure 8:
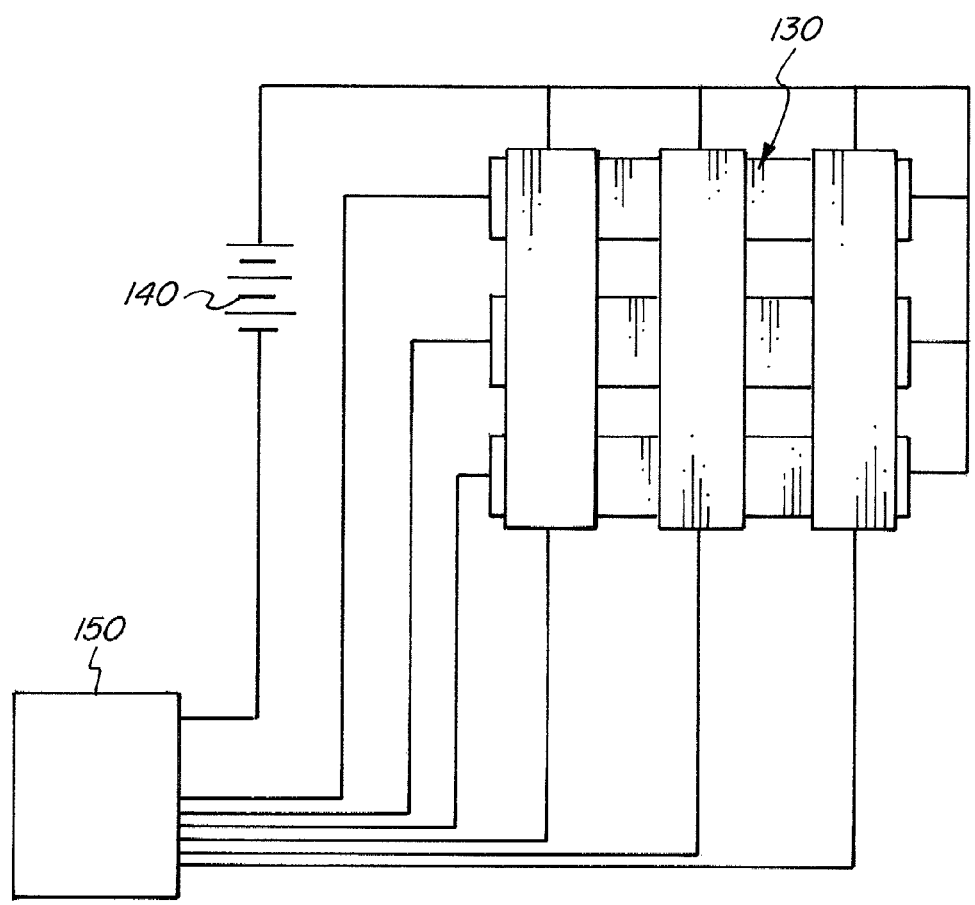
FIG. 8 is schematic diagram depicting use of the tensiometer in a circuit.

Referring now to FIG. 8, shown is a schematic diagram depicting use of the patch design tensiometer 130 in a circuit. The circuit may be adapted for measuring conductivity across the tensiometer. A power source 140 may provide current to the patch design tensiometer 130 and the returning current may then be sent to a processor 150, although not limited thereto. Based on the changing conductivity of the patch design tensiometer 130, changes in stretch in a number of different directions can be measured by the circuit. It is appreciated that the circuit could designed in any number of different ways, including with the use of discrete components such as the processor 150 as shown, an integrated circuit, or any other form of technology capable of measuring the conductivity of the tensiometer, and the present teachings are not limited to this particular embodiment. In one embodiment, the processor 150 may be in wireless communication with the circuit, although not limited thereto.

Figure 9:
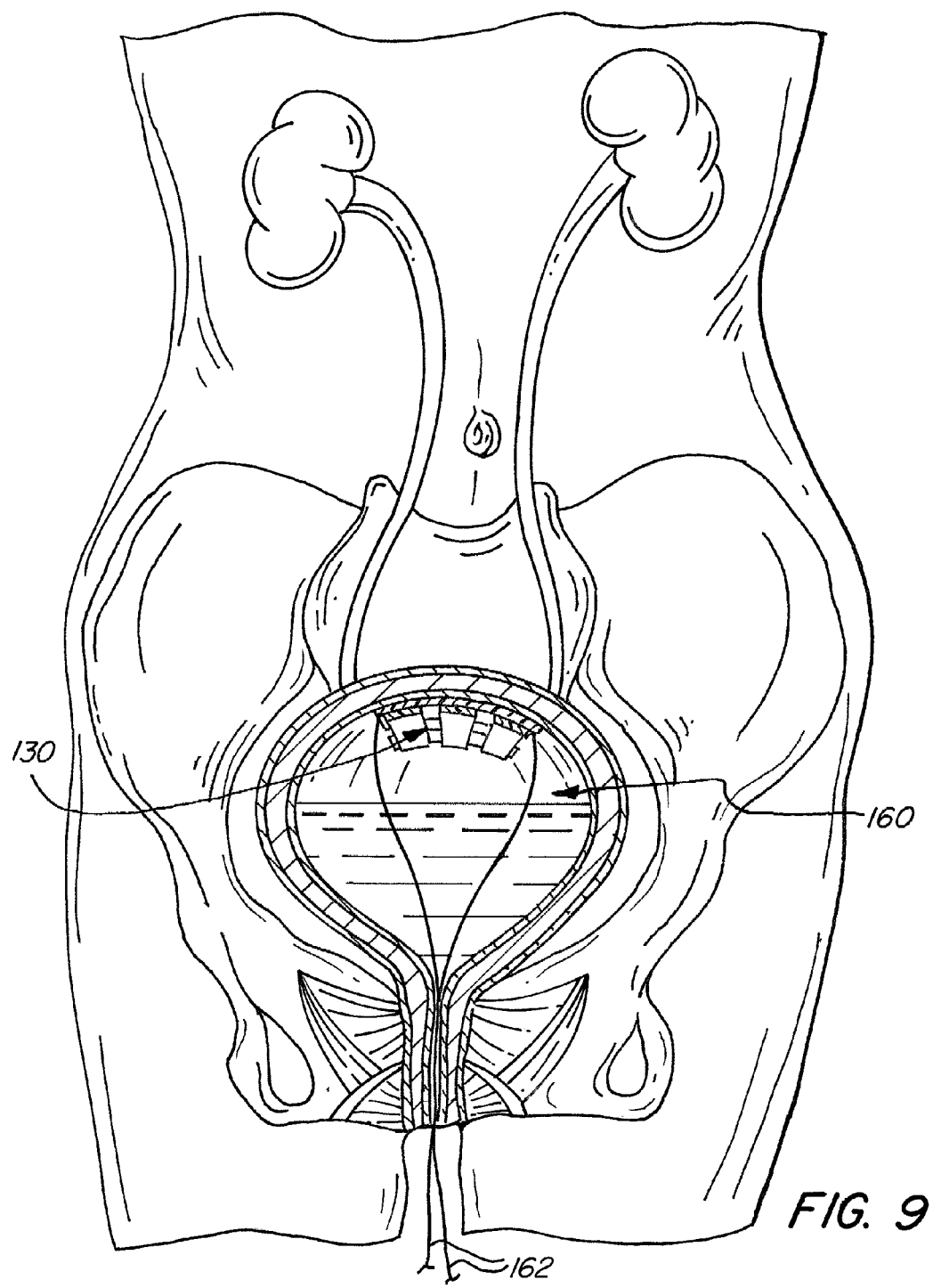
FIG. 9 is an illustration depicting the tensiometer implanted into a human bladder.

The tensiometer may be affixed to the dome or stretched around the circumference of the bladder, although not limited thereto. Referring now to FIG. 9, shown is an illustration depicting the patch design tensiometer 130 implanted into a human bladder 160. The tensiometer could measure bladder wall tension as the bladder expands and contracts. Anchors may be used to secure the tensiometer to the bladder wall.

The tensiometer may be attached to a signaling device to notify the patient of the state of bladder fullness. It could also be interfaced with existing technology, such as the InterStim™ sacral nerve stimulator, or any future technology. Flexible wire 162 could connect the patch design tensiometer 130 to create a circuit with a battery and recording chip to signal when catheterization is needed. A recording chip may be helpful to show measurements over time. Alternatively, a gauge could be attached to directly display bladder tension. Wireless connectivity may also be incorporated, or there could be an interface similar to cochlear implants.

The power source may be similar to existing implantable devices (e.g., permanent pacemakers, implantable nerve stimulators, etc.). For example, the InterStim™ sacral nerve stimulator has a battery life of 2.9 to 5.4 years. As such, the tensiometer could be implanted for long periods of time. In the alternative, the tensiometer may be powered by an external power source, or even by bioactivity, and the present teachings are not limited to these particular embodiments.

The tensiometer could also be placed outside of the bladder on its upper surface/dome, although not limited thereto. This would require surgical placement. However, if placed within the bladder cavity, as is shown in FIG. 9, placement of the tensiometer may not require surgery as the tensiometer could be inserted via the urethra/cystoscopically. It is appreciated that the tensiometer could be designed in any number of different shapes and sizes for particular purposes and a single strip/strand, measuring tension along just one dimension, may be preferable for non-surgical placement in the bladder. Flexible wire 162 coming out the urethra externally could be done for a short term application, but may be impractical longer term.

The tensiometer is also ideal for incorporation into medical devices that assess tissue tension. One potential use is to monitor the stretching of skin by tissue expanders. Tissue expanders are placed beneath the skin and gradually inflated with a solution in order to increase its volume. This increases the surface area of available skin for reconstructive surgical procedures. The tensiometer may be used to assure that the expanded skin is not under excessive tension, which could increase the risk of injury. Uses in the laboratory for the tensiometer are also possible in various animal models.

Another potential application is to measure the tension of the pelvic floor muscles, especially the urethral sphincter. With only a small incision and local anesthesia, the tensiometer could be easily implanted and removed. This would be very helpful for patients with Fowler's syndrome, for example, in which the sphincter cannot open because of abnormal muscle activity, causing contractions instead of relaxation. The current way to measure muscle tension indirectly is with a cumbersome patch or a needle electromyogram (EMG) which only stays on for short periods of time, is uncomfortable, and must be performed in a hospital setting. Muscle tension may be studied with the tensiometer by affixing it to a muscle to monitor intramuscular tension.

There are also many nonmedical applications of the tensiometer for measuring dynamic tension. Although particular exemplary uses have been discussed here in detail, these are meant to be instructive and the present teachings are not limited to these particular embodiments. In fact, anywhere where it would be desirable to measure surface movement is a potential application for the tensiometer. While it has been described for measuring stretch and tension, it could also be utilized to measure any deformation of shape including, but not limited to, pressure, stretching, twisting, and compression.

Figure 10:
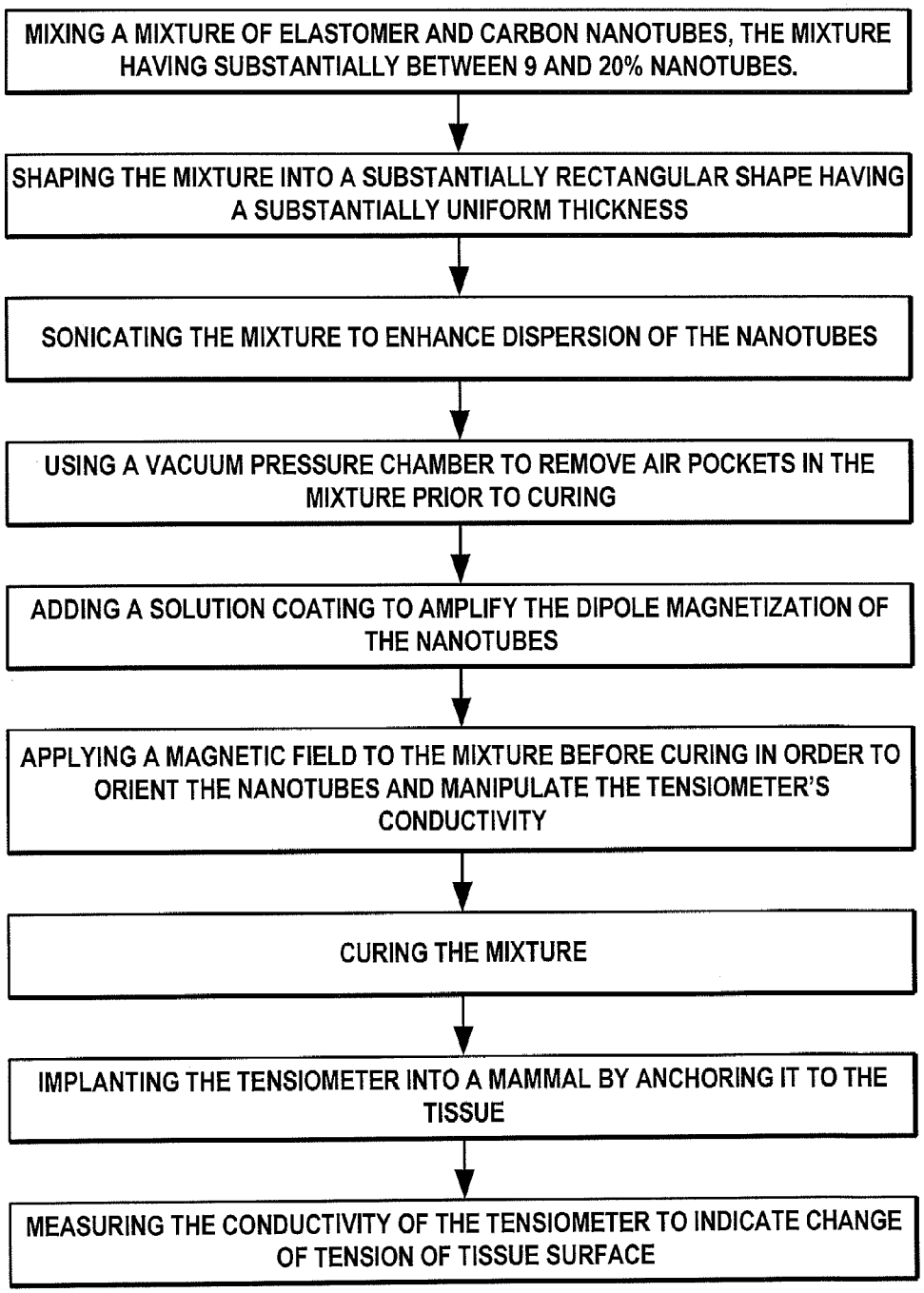
FIG. 10 is a flowchart depicting one embodiment of the processes for making and using the tensiometer according to the present teachings.

Referring now to FIG. 10, shown is a flowchart depicting one embodiment of the processes for making and using the tensiometer according to the present teachings. The following steps may be performed for making the tensiometer, although not limited thereto: mixing a mixture of elastomer and carbon nanotubes, the mixture having substantially between 9 and 20% nanotubes, which may be measured by weight; shaping the mixture into a substantially rectangular shape having a substantially uniform thickness; sonicating the mixture to enhance dispersion of the nanotubes; and curing the mixture; wherein the conductivity of the tensiometer increases as the tensiometer is stretched along an axis, the tensiometer is non-toxic and suitable for implanting in a mammal, and the tensiometer has a reproducible conductivity suitable for measuring changes to the tensiometer's stretch by corresponding changes in the tensiometer's conductivity.

The method of manufacturing may further comprise the step of applying a magnetic field to the mixture before curing in order to orient the nanotubes and manipulate the tensiometer's conductivity. The method may further comprise the step of adding a solution coating to amplify the dipole magnetization of the nanotubes. It is appreciated that these steps may be performed at any point before the curing step has completed.

The method of manufacturing may further comprise the step of using a vacuum pressure chamber to remove air pockets in the mixture prior to curing. In one embodiment, the step of shaping may comprise drop casting the mixture on glass or compressing the mixture between glass plates. In another embodiment, the step of curing may comprise adding a catalyst to accelerate polymerization.

The following steps may be performed for using the tensiometer, although not limited thereto: implanting the tensiometer into a mammal by anchoring it to tissue; and measuring the conductivity of the tensiometer to indicate change of tension of tissue surface. The tensiometer may comprise, although not limited thereto: a mixture of an elastomer and carbon nanotubes, the mixture having substantially between 9 and 20% nanotubes by weight, and a circuit adapted for measuring conductivity across the tensiometer, wherein the conductivity of the tensiometer increases as the tensiometer is stretched along an axis, the tensiometer has reproducible conductivity suitable for measuring changes to the tensiometer's stretch by corresponding changes in the tensiometer's conductivity, and the tensiometer is non-toxic and suitable for implanting in a mammal for measuring change in tension.

In one embodiment, the method of using the tensiometer may measure change in tension of a bladder. The method may measure change in tension of pelvic floor muscles. The method may measure change in tension of a stomach. The method may measure change in tension of a sphincter. The method may measure change in tension of an epidermis.

While the present teachings have been described above in terms of specific embodiments, it is to be understood that they are not limited to these disclosed embodiments. Many modifications and other embodiments will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:

1. A tensiometer comprising:
 a mixture of an elastomer and carbon nanotubes, the mixture having substantially between 9% and 20% nanotubes by weight, and
 a circuit adapted for measuring conductivity across the tensiometer, the circuit having a power source capable of being implanted into a mammal,
 wherein the conductivity of the tensiometer increases as the tensiometer is stretched along an axis,
 the tensiometer has reproducible conductivity suitable for measuring changes to the tensiometer's stretch by corresponding changes in the tensiometer's conductivity,
 the tensiometer is non-toxic and suitable for implanting in a mammal, and
 the tensiometer is capable of being secured to tissue on the inside of a mammal for measuring tissue tension.

2. The tensiometer of claim 1 wherein the tensiometer is substantially rectangular in shape.

3. The tensiometer of claim 1 further comprising a second tensiometer having an axis that is offset from the axis of the first tensiometer.

4. The tensiometer of claim 3 wherein the tensiometer has a cross-hatched shape such that the tensiometer is suitable for measuring changes in tension in more than one direction.

5. The tensiometer of claim 1 wherein the mixture comprises substantially between 14 and 16% nanotubes by weight.

6. The tensiometer of claim 1 further comprising computer readable media for recording changes in tension.

7. The tensiometer of claim 1 further comprising a processor for receiving conductivity information wherein the circuit connects wirelessly with the processor.

8. The tensiometer of claim 1 wherein the nanotubes are multi-walled.

9. The tensiometer of claim 1, wherein the tensiometer is capable of being secured to the wall of a human bladder for measuring bladder wall tension.

10. The tensiometer of claim 9 further comprising a signaling device to notify of bladder fullness.

11. The tensiometer of claim 9 further comprising an implantable neural stimulator for improved bladder control.

12. The tensiometer of claim 1 further comprising anchors to secure the tensiometer to the tissue.

13. The tensiometer of claim 1, wherein the tensiometer is used with a tissue expander to measure the tension of expanded skin.

14. The tensiometer of claim 1, wherein the tensiometer is capable of being secured to pelvic floor muscles.

15. The tensiometer of claim 1, wherein the tensiometer is capable of being secured to a sphincter.

16. The tensiometer of claim 1, wherein the tensiometer is capable of being secured to a stomach.

17. A method of using a tensiometer, the tensiometer comprising:
   a mixture of an elastomer and carbon nanotubes, the mixture having substantially between 9% and 20% nanotubes by weight, and
   a circuit adapted for measuring conductivity across the tensiometer, the circuit having a power source capable of being implanted into a mammal,
   wherein the conductivity of the tensiometer increases as the tensiometer is stretched along an axis,
   the tensiometer has reproducible conductivity suitable for measuring changes to the tensiometer's stretch by corresponding changes in the tensiometer's conductivity, and
   the tensiometer is non-toxic and suitable for implanting in a mammal, and
   the tensiometer is capable of being secured to tissue on the inside of a mammal for measuring tissue tension,
   the method comprising the steps of:
   implanting the tensiometer into a mammal by anchoring the tensiometer to tissue, and
   measuring the conductivity of the tensiometer to indicate change of tension of tissue surface.

18. The method of claim 17 wherein the tensiometer measures change in tension of a bladder.

19. The method of claim 17 wherein the tensiometer measures change in tension of pelvic floor muscles.

20. The method of claim 17 wherein the tensiometer measures change in tension of a stomach.

21. The method of claim 17 wherein the tensiometer measures change in tension of a sphincter.

22. The method of claim 17 wherein the tensiometer measures change in tension of an epidermis.

23. A method of manufacturing a tensiometer, comprising the steps of:
   mixing a mixture of elastomer and carbon nanotubes, the mixture having substantially between 9% and 20% nanotubes by weight,
   shaping the mixture into a substantially rectangular shape having a substantially uniform thickness,
   sonicating the mixture to enhance dispersion of the nanotubes, and
   curing the mixture,
   connecting the mixture to a circuit adapted for measuring conductivity across the tensiometer, the circuit having a power source capable of being implanted into a mammal,
   wherein the conductivity of the tensiometer increases as the tensiometer is stretched along an axis,
   the tensiometer is non-toxic and suitable for implanting in a mammal,
   the tensiometer has a reproducible conductivity suitable for measuring changes to the tensiometer's stretch by corresponding changes in the tensiometer's conductivity, and
   the tensiometer is capable of being secured to tissue on the inside of a mammal for measuring tissue tension.

24. The method of claim 23 further comprising the step of applying a magnetic field to the mixture before curing in order to orient the nanotubes and manipulate the tensiometer's conductivity.

25. The method of claim 24 further comprising the step of adding a solution coating to amplify the dipole magnetization of the nanotubes.

26. The method of claim 23 further comprising the step of using a vacuum pressure chamber to remove air pockets in the mixture prior to curing.

27. The method of claim 23 wherein the step of shaping comprises drop casting the mixture on glass or compressing the mixture between glass plates.

28. The method of claim 23 wherein the step of curing comprises adding a catalyst to accelerate polymerization.

* * * * *